United States Patent [19]

Yang

[11] 4,285,881

[45] Aug. 25, 1981

[54] DIOXANE REMOVAL FROM ETHER SULFATE

[75] Inventor: Kang Yang, Ponca City, Okla.

[73] Assignee: Conoco, Inc., Ponca City, Okla.

[21] Appl. No.: 138,052

[22] Filed: Apr. 7, 1980

[51] Int. Cl.$^3$ .......................................... C07C 141/02
[52] U.S. Cl. .............................. 260/458 R; 260/340.6; 260/458 C
[58] Field of Search ............. 260/458 R, 458 C, 340.6

[56] References Cited

U.S. PATENT DOCUMENTS

B 466,304  3/1976  Wolf et al. .................... 260/340.6 X

OTHER PUBLICATIONS

K. L. Mittal, Editor, "Solution Chemistry of Surfactants", vol. 1, Plenum Publ. Corp., 1979, pp. 195–218.

*Primary Examiner*—Nicky Chan
*Attorney, Agent, or Firm*—Cortlan R. Schupbach, Jr.

[57] ABSTRACT

Dioxane impurities in ether sulfates are removed by using a novel steam stripping technique in which water is neither added to nor removed from ether sulfate. This is possible because the chemical potential of water in the vapor phase is kept at the same value as that of water in the solution phase. In this way, thickening and foaming are avoided while dioxane levels can be reduced to below 10 parts per million by weight in a single pass.

6 Claims, 1 Drawing Figure

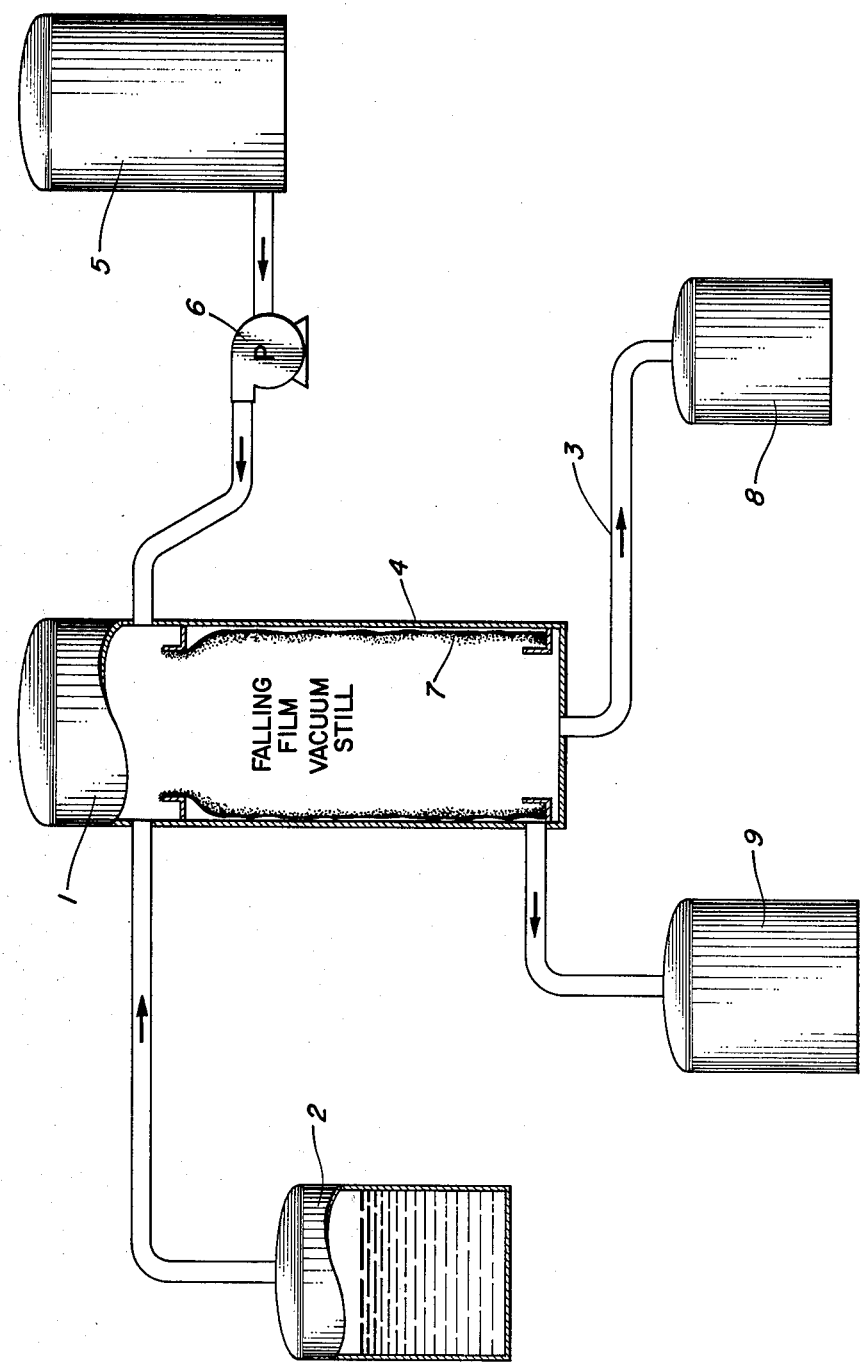

DIOXANE REMOVAL FROM ETHER SULFATE

This invention relates to a method for selectively removing dioxane from an ether sulfate/dioxane mixture. More specifically, this invention relates to a method for selectively removing dioxane from an ether sulfate/dioxane mixture by contacting the ether sulfate/dioxane mixture with dioxane free water vapor and adjusting the chemical potential of the two immiscible phases to selectively absorb the dioxane component from the ether sulfate.

Ether sulfates are usually prepared by the sulfation of alcohol ethoxylates according to the formula

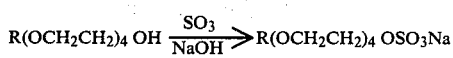

Sulfating agents can vary and include $SO_3$, chlorosulfonic acid and sulfamic acid. A variety of neutralizing agents can be used, such as sodium hydroxide, ammonia and magnesium hydroxide. However, these materials normally enter into side reactions and produce dioxane, a material which is undesirable since it is potentially harmful to humans even in low amounts, and since the majority of detergents are used in a human environment.

Dioxane removal from ether sulfates has been a problem when separations are carried out by methods such as extraction, fractional distillation, precipitation and so forth, the problems have arisen. For example, when an attempt is made to use distillation-like techniques such as azeotropic distillation, vacuum stripping and the like to remove dioxane from commercial ether sulfates, there occurs a sudden increase in ether sulfate viscosity which makes subsequent processing very difficult. In addition, excessive foaming can occur to further compound the problem. Commercial ether sulfates, for example, can contain high concentrations of dioxanes (above about 1000 parts per million by weight) which is unacceptable.

Thus an economical process for removing this impurity is needed. In addition, the process should provide a means for recovering dioxane for subsequent use.

Dioxane is a valuable material in use areas such as solvents and paint production. Recovery of dioxane would therefore also be useful.

It is therefore an object of the present invention to provide a separation technique which allows dioxane to be removed from ether sulfates without hindering the further processability of said ether sulfates. Other objects will become apparent to those skilled in this art as the description proceeds.

It has now been discovered according to the present invention that dioxane can be removed from ether sulfates by contacting a mixture of ether sulfates and dioxane with dioxane-free water vapor at temperatures ranging from about 25° C. to about 150° C. Using this technique, water is neither added to or removed from ether sulfates since both the ether sulfate/dioxane mixture and the water vapor are at the same temperature maintaining the chemical potential of water in vapor phase at essentially the same value as that in solution phase. In this way, it is possible to circumvent the processing difficulties of thickening and foaming encountered in conventional steam stripping. Water containing dioxane which exits the process can be treated to remove dioxane by any of several methods known to the art. Dioxane recovered from the water is suitable for normal uses, such as solvent.

In the context of the present invention, the term "chemical potential" and "adjusted chemical potential" mean the relative affinity of dioxane for the water vapor passing over the ether sulfate. This chemical potential is usually adjusted simply by altering at least one of two main parameters concentration and temperature. In practice, it is desired that the ether sulfate/dioxane mixture be contacted with an immiscible water vapor phase which contains substantially no dioxane, and adjusting the chemical potential of the water vapor phase such that rapid removal of dioxane from the ether sulfate will occur. In essence, the affinity of dioxane for water vapor is vastly increased by such adjustment. This contact is normally carried out using thin film techniques such that a maximum surface area is exposed to the water vapor phase which has the adjusted chemical potential. In general, thin film stills can be altered to carry out such removals.

Representative examples of apparatus which can be adjusted to carry out the method of the instant invention are Luwa thin film evaporator, trademark of and sold by Luwa Corp., Charlotte, N.C.; Kontrol thin film still, trademark of and sold by Kontrol Company, Athol Md., and thin film evaporators produced by Arthur Smith Corporation, Pompano Beach, Fla.

The instant invention is carried out at temperatures of from about 25° C. to about 150° C. However, these temperatures can be altered if the pressure in the still is likewise altered. For example, pressure in the still will require a higher temperature, whereas pulling a partial vacuum on the still will allow lower temperatures to be used.

BRIEF DESCRIPTION OF THE DRAWING

The drawing describes graphically a Asco Model 50-2 still which has modified to function as a falling film evaporator. The cold finger assembly normally attached to the unit was removed, and the resulting opening was used as a low pressure steam inlet (1). The stream of low pressure steam was generated by connecting a heated water reservoir (2) to house vacuum (3). The temperature of the water reservoir was maintained at the same value as the temperature in the stripping column itself (4). In this manner the chemical potential gradient between the steam phase and the sulfate phase was essentially eliminated. Ether sulfate/dioxane mixtures were obtained commercially, (as sold by Conoco Inc.) and were pumped from a reservoir (5) through a pump (6) into the still (4). The still is designed to operate using a falling film (7) in the column. Ether sulfate was collected in a cold trap (9) while water containing dioxane was collected at the bottom of the still in a condenser (8).

The invention is more concretely described with reference to the examples below wherein all parts and percentages are by weight unless otherwise specified. Examples are provided to illustrate the instant invention and not to limit it.

EXAMPLE 1

An Asco still (trademark of and sold by Arthur Smith Company—Model 50-2) was modified to function as a falling film stripper as described in the figure. The temperature of the water saturator for air was maintained at the same value as that of the stripping column, eliminating the chemical potential gradient between ether sulfate and air such that no net transfer of water occurs (both phases have substantially the same water content exiting the process as when introduced into the process).

An ether sulfate sample containing 1204 parts per million by weight (ppmw) dioxane was passed through the apparatus over a 60 minute period. The ether sulfate contained 40% water. During the same period of time, 10 grams of steam was passed through the column. A single pass operation at 65° C. reduced dioxane content in the ether sulfate from 1204 ppmw to 74 ppmw.

EXAMPLE 2

An experiment was carried out exactly as described in Example 1 except that a ether sulfate containing only 142 ppmw was passed through the apparatus under the same conditions where the ether sulfate contained 40% water. A single pass operation at 65° C. over a 60 minute period reduced dioxane from 142 ppmw to 8 ppmw.

Time of contact is important in that contact between the dioxane-free steam and the ether sulfate containing dioxane must be maintained for a time sufficient to remove substantially all dioxane. Normally this contact will be carried out for a period of time ranging from about 10 seconds to about 10 hours, although from about 5 minutes to about 1 hour is usually adequate. It is usually desired to reduce dioxane contents to below about 10 ppmw.

Maximized surface area is important to the concept of the present invention. Residence time in the apparatus must be lengthened if the surface area of the ether sulfate dioxane mixture is reduced.

Thus the present invention provides a novel, efficient and simple method for carrying out the removal of dioxane from ether sulfates while avoiding foaming and thickening problems encountered in prior art methods.

While certain embodiments and details have been shown for the purpose of illustrating this invention, it will be apparent to those skilled in this art that various changes and modifications may be made herein without departing from the spirit or scope of the invention.

I claim:

1. A method for removal of dioxane from ether sulfates comprising contacting ether sulfates/dioxane mixtures with dioxane-free water vapor at temperatures of from about 25° C. to about 150° C.

2. A method as described in claim 1 wherein the ether sulfate containing dioxane is contacted as a flowing film by water vapor.

3. A method as described in claim 2 wherein the contact is carried out for a time sufficient to remove substantially all dioxane.

4. A method as described in claim 3 wherein the contact is carried out for a period of time ranging from about 10 seconds to about 10 hours.

5. A method as described in claim 4 wherein the dioxane content of ether sulfates is reduced below about 10 parts per million by weight.

6. A method as described in claim 1 wherein the ether sulfates are prepared by the sulfation of alcohol ethoxylates.

* * * * *